(12) United States Patent
Narimatsu (10) Patent No.: US 6,699,197 B2
(45) Date of Patent: Mar. 2, 2004

(54) PULSE-WAVE-PROPAGATION-VELOCITY-RELATED-INFORMATION OBTAINING APPARATUS

(75) Inventor: Kiyoyuki Narimatsu, Komaki (JP)

(73) Assignee: Colin Corporation, Komaki (JP)

(*) Notice: Subject to any disclaimer, the term of this patent is extended or adjusted under 35 U.S.C. 154(b) by 0 days.

(21) Appl. No.: 10/073,025

(22) Filed: Feb. 12, 2002

(65) Prior Publication Data

US 2003/0004420 A1 Jan. 2, 2003

(30) Foreign Application Priority Data

Jul. 2, 2001 (JP) .................................... 2001-200503

(51) Int. Cl.[7] .............................................. A61B 5/02
(52) U.S. Cl. ........................ 600/500; 600/485; 600/481
(58) Field of Search ................................ 600/485, 481, 600/490–495, 500–504, 506, 507

(56) References Cited

U.S. PATENT DOCUMENTS

| 5,183,051 A | * | 2/1993 | Kraidin et al. ............... 600/500 |
| 5,309,916 A | * | 5/1994 | Hatschek .................... 600/485 |
| 5,497,779 A | | 3/1996 | Takaya et al. |
| 5,743,856 A | | 4/1998 | Oka et al. |

FOREIGN PATENT DOCUMENTS

| DE | 198 18 147 C1 | 4/1998 |
| JP | A 9-122091 | 5/1997 |

* cited by examiner

Primary Examiner—Robert L. Nasser
Assistant Examiner—Patricia Mallari
(74) Attorney, Agent, or Firm—Oliff & Berridge, PLC (57) ABSTRACT

An apparatus for obtaining information related to a velocity at which a pulse wave propagates in a living subject, the apparatus including a pulse-wave sensor which is adapted to be worn on a body portion of the subject and detects the pulse wave from the body portion, an incident-wave-peak determining device for determining a peak of an incident-wave component which is contained in the pulse wave detected by the pulse-wave sensor, a reflected-wave-peak determining device for determining a peak of a reflected-wave component which is contained in the pulse wave detected by the pulse-wave sensor, and an information obtaining device for obtaining the information based on a time difference between the peak of the incident-wave component determined by the incident-wave-peak determining device and the peak of the reflected-wave component determined by the reflected-wave-peak determining device.

9 Claims, 8 Drawing Sheets

FIG. 8 a pulse-wave-propagation-velocity-related-information obtaining apparatus which can obtain pulse-wave-propagation-velocity-related information, with a single heartbeat-synchronous-signal detecting device (e.g., a pulse-wave sensor) worn on a living subject.

PULSE-WAVE-PROPAGATION-VELOCITY-RELATED-INFORMATION OBTAINING APPARATUS

BACKGROUND OF THE INVENTION

1. Field of the Invention

The present invention relates to a pulse-wave-propagation-velocity-related-information obtaining apparatus for obtaining information (e.g., a pulse-wave propagation time or a pulse-wave propagation velocity) that is related to a velocity at which a pulse wave propagates in a living subject.

2. Related Art Statement

Arteriosclerosis is known as a factor that influences pulse-wave-propagation-velocity-related information. This is utilized to evaluate a degree of arteriosclerosis of a living subject based on the pulse-wave-propagation-velocity-related information. A pulse-wave propagation time as a sort of pulse-wave-propagation-velocity-related information can be obtained by measuring a time difference between a time of detection of a heartbeat-synchronous signal at one portion of a living subject and a time of detection of the heartbeat-synchronous signal at another portion of the subject. A pulse-wave propagation velocity can be obtained by dividing the pulse-wave propagation time by a distance between the two portions of the subject. For example, an apparatus disclosed in Japanese patent document No. 9-122091 or its corresponding U.S. Pat. No. 5,743,856 detects, as a heartbeat-synchronous signal, an electrocardiographic signal (electrocardiogram) and a brachial pulse wave, and calculates, as a pulse-wave propagation time, a time difference between a time of detection of an R-wave of the electrocardiogram and a time of detection of a peak of the brachial pulse wave.

Since arteriosclerosis is directly related to hypertension, it is desirable that like blood pressure, arteriosclerosis be routinely measured at home. However, in the case where pulse-wave-propagation-velocity-related information is obtained by detecting a heartbeat-synchronous signal at two portions of a living subject, as described above, it is needed to employ and wear two heartbeat-synchronous-signal detecting devices, and yet it is considerably cumbersome to wear the two heartbeat-synchronous-signal detecting devices on the subject. Thus, it has been difficult to routinely measure pulse-wave-propagation-velocity-related information at home.

SUMMARY OF THE INVENTION

It is therefore an object of the present invention to provide a pulse-wave-propagation-velocity-related-information obtaining apparatus which can obtain pulse-wave-propagation-velocity-related information, with a single heartbeat-synchronous-signal detecting device (e.g., a pulse-wave sensor) worn on a living subject.

The Inventor has carried out extensive studies to achieve the above object, and has found that an observed pulse wave (i.e., an observed wave) is a composite wave containing an incident wave produced from the heart of the subject and a reflected wave that is produced from the heart and then reflected at a certain reflection point and that a time difference between the incident-wave component and the reflected-wave component, contained in the composite wave, indicates a time needed for the pulse wave to propagate over a distance equal to twice the distance between the observation point and the reflection point. The present invention has been developed based on those findings.

The above object has been achieved by the present invention. According to the present invention, there is provided an apparatus for obtaining information related to a velocity at which a pulse wave propagates in a living subject, the apparatus comprising (a) a pulse-wave sensor which is adapted to be worn on a body portion of the subject and detects the pulse wave from the body portion, (b) an incident-wave-peak determining means for determining a peak of an incident-wave component which is contained in the pulse wave detected by the pulse-wave sensor, (c) a reflected-wave-peak determining means for determining a peak of a reflected-wave component which is contained in the pulse wave detected by the pulse-wave sensor, and (d) an information obtaining means for obtaining the information based on a time difference between the peak of the incident-wave component determined by the incident-wave-peak determining means and the peak of the reflected-wave component determined by the reflected-wave-peak determining means.

According to the present invention, the incident-wave-peak determining means and the reflected-wave-peak determining means determine the respective peaks of the incident-wave and reflected-wave components of the pulse wave detected by the pulse-wave sensor, and the information obtaining means obtains the information based on a time difference between the peak of the incident-wave component and the peak of the reflected-wave component. Thus, the present apparatus can obtain, with the single pulse-wave sensor, the pulse-wave-propagation-velocity-related information.

According to a preferred feature of the present invention, the obtaining apparatus further comprises an arteriosclerosis-degree determining means for determining a degree of arteriosclerosis of the subject, based on the information obtained by the information obtaining means, according to a prescribed relationship between degree of arteriosclerosis and information related to velocity of propagation of pulse wave. Thus, the present apparatus directly evaluates a hardness of arteries of the subject as the degree of arteriosclerosis determined by the arteriosclerosis-degree determining means.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
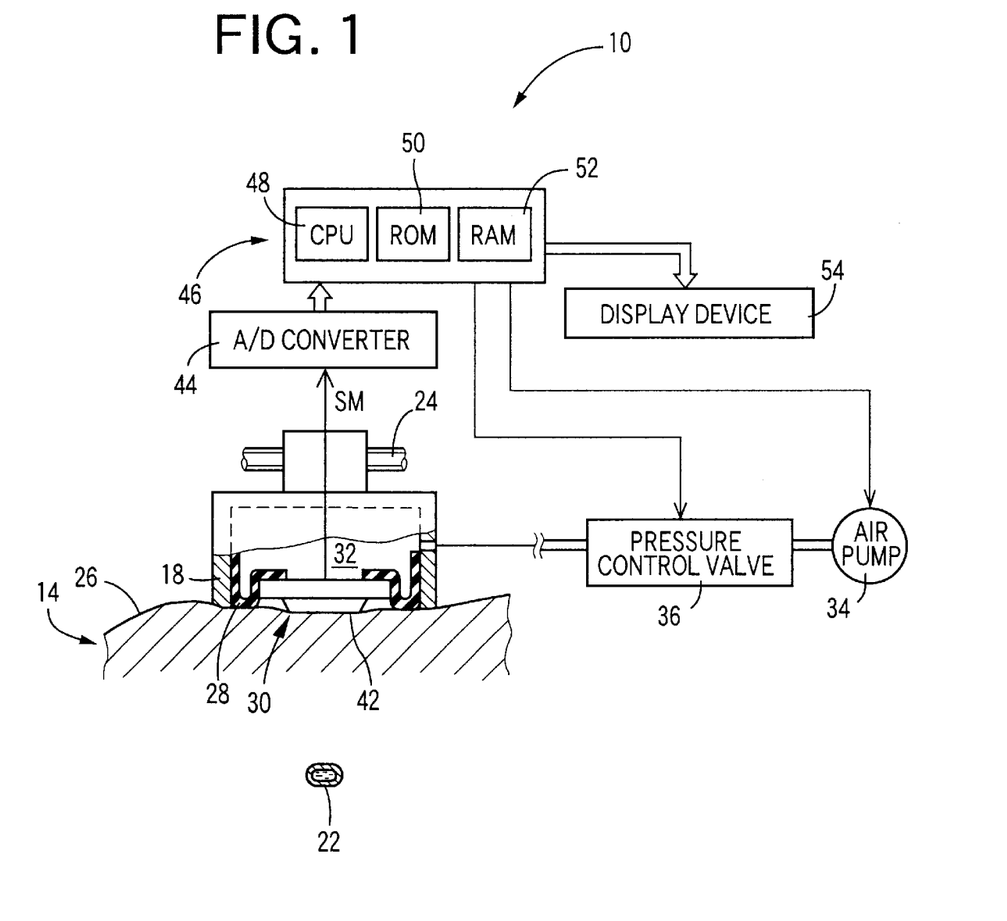
FIG. 1 is a diagrammatic view showing a circuitry of a pulse-wave-propagation-velocity-related-information obtaining apparatus to which the present invention is applied.

Hereinafter, there will be described an embodiment of the present invention in detail by reference to the drawings. FIG. 1 is a diagrammatic view showing a circuitry of a pulse-wave-propagation-velocity-related-information obtaining apparatus 10 to which the present invention is applied. The present apparatus 10 includes a pressure-pulse-wave detecting probe 12 shown in FIG. 2.

Figure 2:
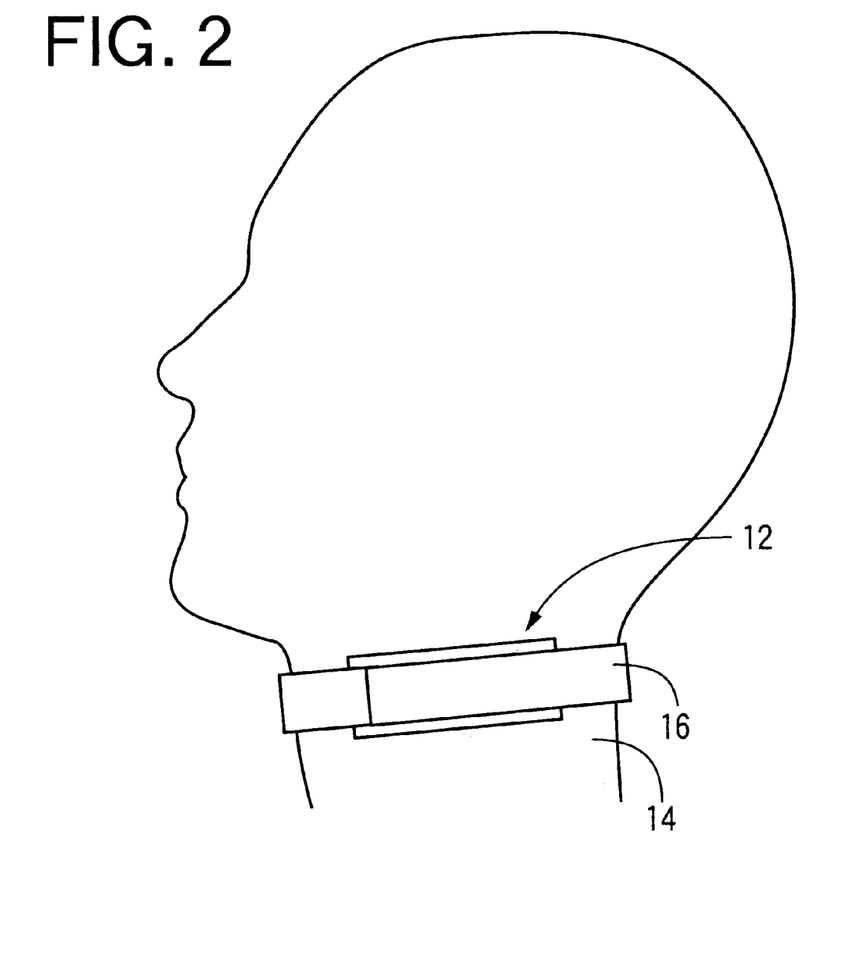
FIG. 2 is an illustrative view showing a state in which a pressure-pulse-wave detecting probe of the apparatus of FIG. 1 is worn on a neck of a living subject.

The pressure-pulse-wave detecting probe 12 is worn on a neck 14 of a living subject, as illustrated in FIG. 2, with the help of a band 16. As shown in detail in FIG. 3, the pressure-pulse-wave detecting probe 12 includes a container-like sensor housing 18; a case 20 which accommodates the sensor housing 18; and a feed screw 24 which is threadedly engaged with the sensor housing 18 and is rotated by an electric motor, not shown, provided in the case 20 so as to move the sensor housing 18 in a widthwise direction of a carotid artery 22. With the help of the band 16, the pressure-pulse-wave detecting probe 12 is detachably attached to the neck 14, such that an open end of the sensor housing 18 is opposed to a body surface 26 of the neck 14.

Figure 3:
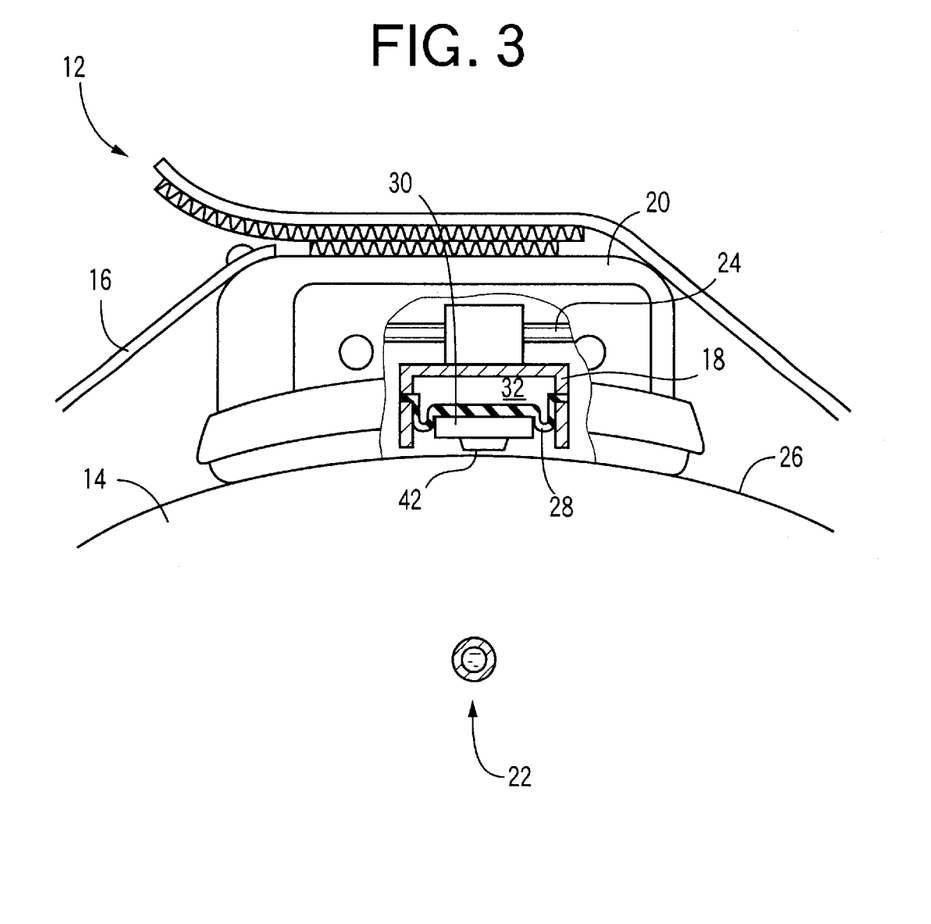
FIG. 3 is an enlarged view of the pressure-pulse-wave detecting probe of FIG. 2, a portion of the probe being cut away.

In addition, the pressure-pulse-wave detecting probe 12 includes a pressure-pulse-wave sensor 30 which is secured via a diaphragm 28 to an inner wall of the sensor housing 18, such that the sensor 30 is movable relative to the housing 18 and is advanceable out of the open end of the same 18. The sensor housing 18, the diaphragm 28, etc. cooperate with one another to define a pressure chamber 32, which is supplied with a pressurized air from an air pump 34 via a pressure-control valve 36, as shown in FIG. 1, so that the pressure-pulse-wave sensor 30 is pressed against the body surface 26 with a pressing force corresponding to the air pressure (Pa) in the pressure chamber 30. Thus, the pressing force applied to the sensor 30 is expressed in terms of the air pressure (mmHg) in the pressure chamber 32.

The sensor housing 18 and the diaphragm 28 cooperate with each other to provide a pressing device 38 which presses the pressure-pulse-wave sensor 30 against the carotid artery 22, and the feed screw 24 and the not-shown motor cooperate with each other to provide a widthwise-direction moving device 40 which moves the pressure-pulse-wave sensor 30 in the widthwise direction of the carotid artery 22 and thereby changes a pressing position where the sensor 30 is pressed on the body surface 26.

Figure 4:
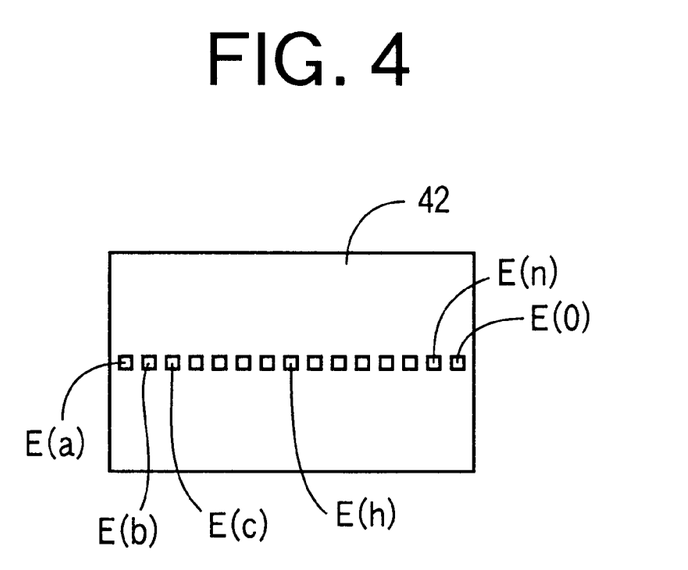
FIG. 4 is a view for explaining a state in which an array of pressure-sensing elements is provided in a press surface of a pressure-pulse-wave sensor shown in FIG. 1.

The pressure-pulse-wave sensor 30 has a pressing surface 42, and a number of semiconductor pressure-sensing elements (hereinafter, referred to as the "pressure-sensing elements") E which are arranged in the pressing surface 42 at a regular interval in the widthwise direction of the carotid artery 22, i.e., in the direction of movement of the sensor 30 parallel to the feed screw 24, over a length greater than the diameter of the carotid artery 22. For example, as shown in FIG. 4, fifteen semiconductor pressure-sensing elements E(a), E(b), . . . , E(o) are arranged at a regular interval of, e.g., 0.6 mm.

Figure 5:
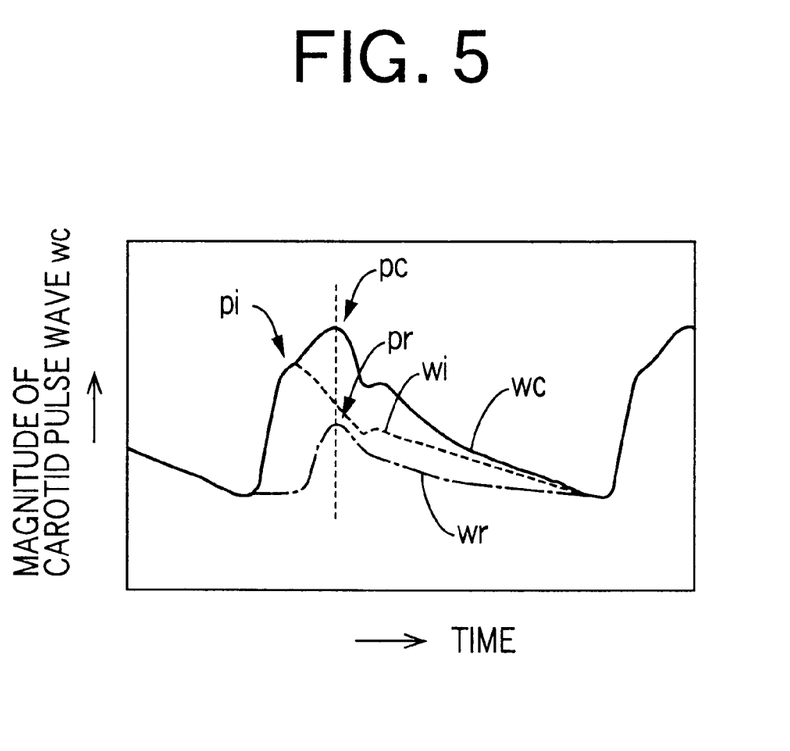
FIG. 5 is a graph showing an example of a carotid pulse wave wc represented by a pressure-pulse-wave signal SM supplied from a pressure-sensing element of the pressure-pulse-wave sensor of FIG. 1.

The pressure-pulse-wave detecting probe 12, constructed as described above, is pressed against the body surface 26 of the neck 14 right above the carotid artery 22, so that the pressure-pulse-wave sensor 30 detects a pressure pulse wave (i.e., a carotid pulse wave, wc) which is produced from the carotid artery 22 and is propagated to the body surface 26, and supplies a pressure-pulse-wave signal SM representing the detected carotid pulse wave wc, to a control device 46 via an A/D (analog-to-digital) converter 44. An example of the carotid pulse wave wc represented by the pressure-pulse-wave signal SM continuously supplied from the pressure-pulse-wave sensor 30 is indicated at solid line in FIG. 5. Since the carotid pulse wave wc is a heartbeat-synchronous signal that is produced in synchronism with heartbeat of the subject, the pressure-pulse-wave detecting probe 12 provides a heartbeat-synchronous-signal detecting device.

The control device 46 is provided by a so-called microcomputer including a central processing unit (CPU) 48, a read only memory (ROM) 50, a random access memory (RAM) 52 and an input-and-output (I/O) port, not shown. The CPU 48 processes signals according to the control programs pre-stored in the ROM 50 by utilizing the temporary-storage function of the RAM 52. In addition, the CPU 48 supplies drive signals via the I/O port to respective drive circuits, not shown, associated with the pressure control valve 36 and the air pump 34 so as to control the pressure in the pressure chamber 32 to an optimum pressing force HDPO, described later. Moreover, the CPU 48 determines a pulse-wave propagation velocity PWV based on the pressure-pulse-wave signal SM supplied from the pressure-pulse-wave sensor 30, and operates a display device 54 to display the thus determined pulse-wave propagation velocity PVW.

Figure 6:
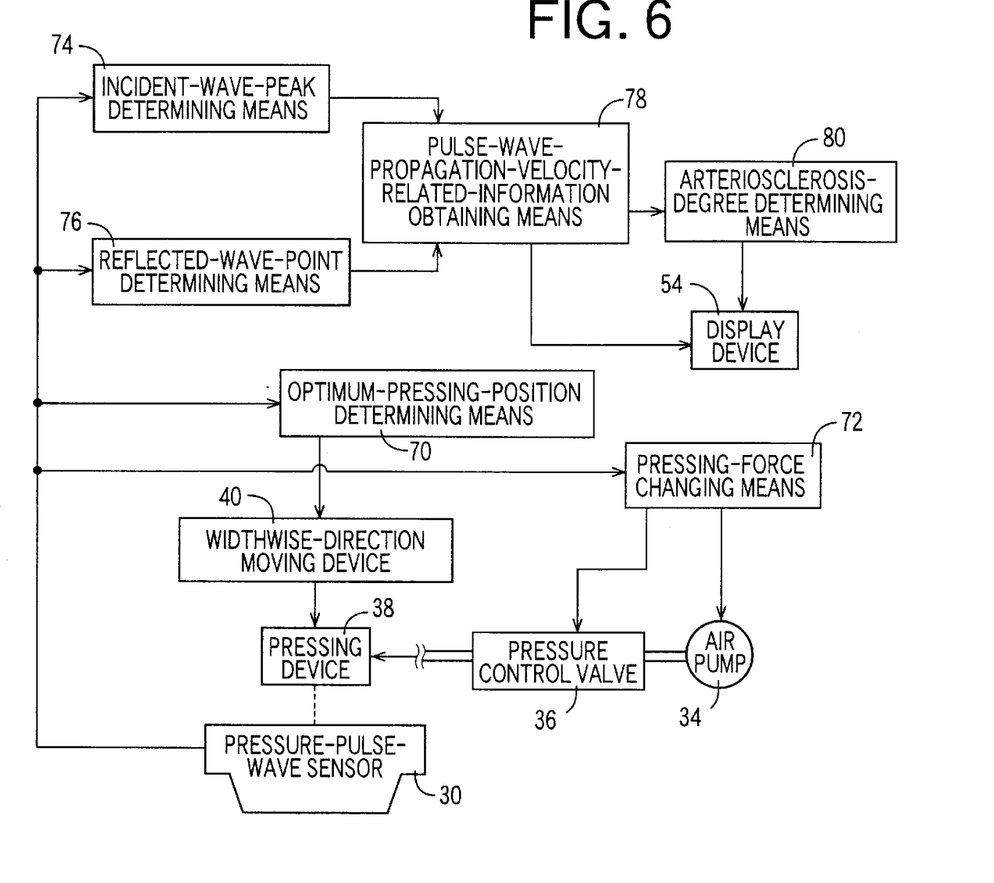
FIG. 6 is a block diagram for explaining essential control functions of a control device of the apparatus of FIG. 1.

FIG. 6 is a block diagram for explaining essential control functions of the control device 46 of the pulse-wave-propagation-velocity-related-information obtaining apparatus 10. An optimum-pressing-position determining means 70 judges whether a prescribed pressing-position changing condition is satisfied, i.e., whether one (hereinafter, referred to as the "highest-pressure detecting element EM") of the pressure-sensing elements E of the pressure-pulse-wave sensor 30 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 22. When this pressing-position changing condition is satisfied, the optimum-pressing-position determining means 70 carries out the following pressing-position changing operation: After the pressing device 38 once moves the pressure-pulse-wave sensor 30 away from the body surface 26, the widthwise-direction moving device 40 moves the pressing device 38 and the sensor 30 over a prescribed distance, and then the pressing device 38 again presses the sensor 30 with a prescribed, considerably low first pressing force HDP1. In this state, the determining means 70 judges again whether the prescribed pressing-position changing condition is satisfied. The determining means 70 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 22) to be pressed by the pressure-pulse-wave sensor 30, and may be one fourth of the diameter.

A pressing-force changing means 72 changes, after the optimum-pressing-position determining means 70 positions the pressure-pulse-wave sensor 30 at the optimum pressing position, a pressing force HDP (i.e., hold-down pressure) applied by the pressing device 38 to the sensor 30, within a prescribed pressing-force range, either stepwise in response to each heartbeat of the subject or continuously at a prescribed, considerably low rate. Based on the carotid pulse wave wc obtained during the changing of the pressing force HDP, the changing means 72 determines an optimum pressing force HDPO and maintains the pressing force applied by the pressing device 38 to the sensor 30, at the thus determined optimum pressing force HDPO. Here, the optimum pressing force HDPO is so determined that a pulse pressure PP of the carotid pulse wave wc detected by the highest-pressure detecting element EM pressed by the pressing force HDP may not be smaller than a predetermined lower-limit pulse pressure $PP_L$. The lower-limit pulse pressure $PP_L$ is experimentally determined as a value which assures that a reference point used to obtain pulse-wave-propagation-velocity-related information can be accurately identified on the carotid pulse wave wc. If the pulse pressure PP is too small, a clear carotid pulse wave wc is not obtained and accordingly accuracy of determination of the reference point on the carotid pulse wave wc is lowered.

An incident-wave-peak determining means 74 successively determines a time of occurrence of a peak, pi, of an incident-wave component, wi, which is contained in each of successive heartbeat-synchronous pulses of the carotid pulse wave wc continuously detected by the highest-pressure detecting element EM of the pressure-pulse-wave sensor 30 in the state in which the pressing force HDP applied to the sensor 30 is maintained at the optimum pressing force HDPO. The carotid pulse wave wc contains the incident-wave component wi, indicated at broken line in FIG. 5, and the peak pi of the incident-wave component wi corresponds to an inflection point or a maximal point of the composite carotid pulse wave wc (i.e., observed wave) that occurs between a rising point and a peak point, pc, of the composite wave wc. In the example shown in FIG. 5, the peak pi of the incident wave wi corresponds to an inflection point of the observed wave wc. To this end, the incident-wave-peak determining means 74 subjects the continuously obtained pressure-pulse-wave signal SM to a prescribed mathematical treatment, to detect an inflection point or a maximal point occurring between a rising point and a peak point pc of each heartbeat-synchronous pulse of the carotid pulse wave wc represented by the signal SM, and determines a time of occurrence of the inflection point or the maximal point as a time of occurrence of the peak pi of the incident wave wi. Here, the mathematical treatment may be a common treatment used to detect an inflection point or a maximal point; such as a differentiation treatment or a filter treatment.

A reflected-wave-peak determining means 76 successively determines a time of occurrence of a peak, pr, of a reflected-wave component, wr, which is contained in each of the successive heartbeat-synchronous pulses of the same carotid pulse wave wc as that on which the incident-wave-peak determining means 74 successively determines the time of occurrence of the peak pi of the incident-wave component wi. The carotid pulse wave wc contains the reflected-wave component wr, indicated at one-dot chain line in FIG. 5, and the peak pr of the reflected-wave component wr corresponds to the peak pc of the observed wave wc. To this end, the reflected-wave-peak determining means 76 detects a peak point pc of each of successive heartbeat-synchronous pulses of the carotid pulse wave wc represented by the continuously obtained pressure-pulse-wave signal SM, and determines a time of occurrence of the peak point pc as a time of occurrence of the peak pr of the reflected wave wr. It is speculated that a main component of the reflected-wave component wr is one which is produced from the heart of the subject and then reflected around an iliac artery of the subject.

A pulse-wave-propagation-velocity-related-information obtaining means 78 successively determines, as a pulse-wave propagation time DT (sec), a time difference between the time of occurrence of the peak pi of the incident-wave component wi successively determined by the incident-wave-peak determining means 74 and the time of occurrence of the peak pr of the reflected-wave component wr successively determined by the reflected-wave-peak determining means 76. Then, the obtaining means 78 successively calculates a pulse-wave propagation velocity PWV (m/sec), i.e., a velocity at which a pulse wave propagates through an artery of the subject, by substituting the thus determined propagation time DT for a parameter, DT, of the following Expression 1:

$$PWV=L/DT \qquad \text{(Expression 1)}$$

The thus calculated pulse-wave propagation velocity PWV is displayed on the display device 54. In Expression 1, symbol L (m) indicates a distance equal to twice the distance between the aortic valve of the subject and the reflection point around the iliac artery of the subject, and is experimentally determined in advance. Each of the pulse-wave propagation time DT and the pulse-wave propagation velocity PWV is obtained as a piece of pulse-wave-propagation-velocity-related information.

Figure 7:
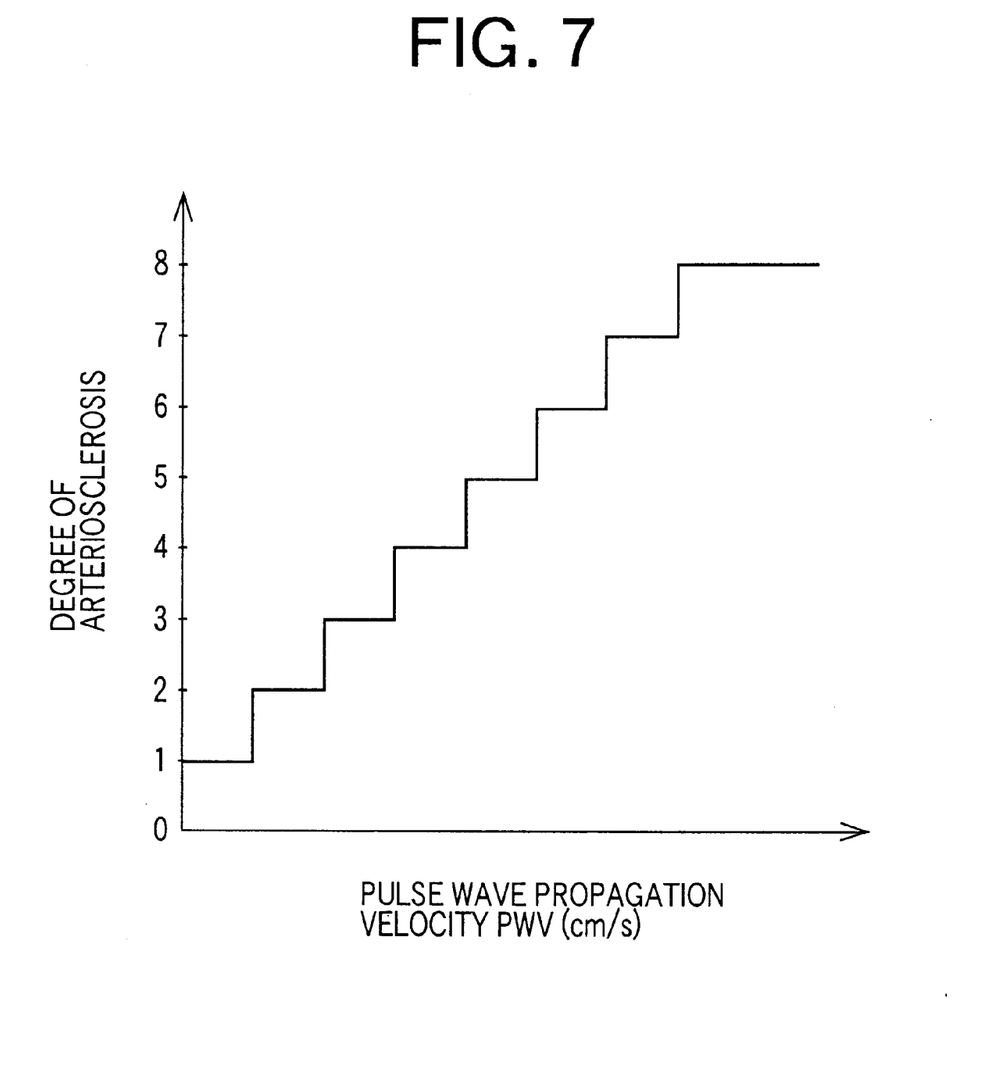
FIG. 7 is a graph showing an example of a prescribed relationship between pulse-wave propagation velocity PWV and degree of arteriosclerosis.

An arteriosclerosis-degree determining means 80 determines a degree of arteriosclerosis of the subject, based on the pulse-wave-propagation-velocity-related information obtained by the pulse-wave-propagation-velocity-related-information obtaining means 78, according to a prescribed relationship between pulse-wave-propagation-velocity-related information and degree of arteriosclerosis, and operates the display device 54 to display the thus determined arteriosclerosis degree. In the case where the pulse-wave propagation velocity PWV is obtained as the pulse-wave-propagation-velocity-related information, the determining means 80 employs a relationship in which, as the pulse-wave-propagation-velocity-related information increases, the degree of arteriosclerosis increases; and in the case where the pulse-wave propagation time DT is obtained as the pulse-wave-propagation-velocity-related information, the determining means 80 employs another relationship in which, as the pulse-wave-propagation-velocity-related information decreases, the degree of arteriosclerosis increases. In either case, the relationship is experimentally determined in advance. FIG. 7 shows an example of a prescribed relationship between pulse-wave-propagation velocity PWV and degree of arteriosclerosis.

Figure 8:
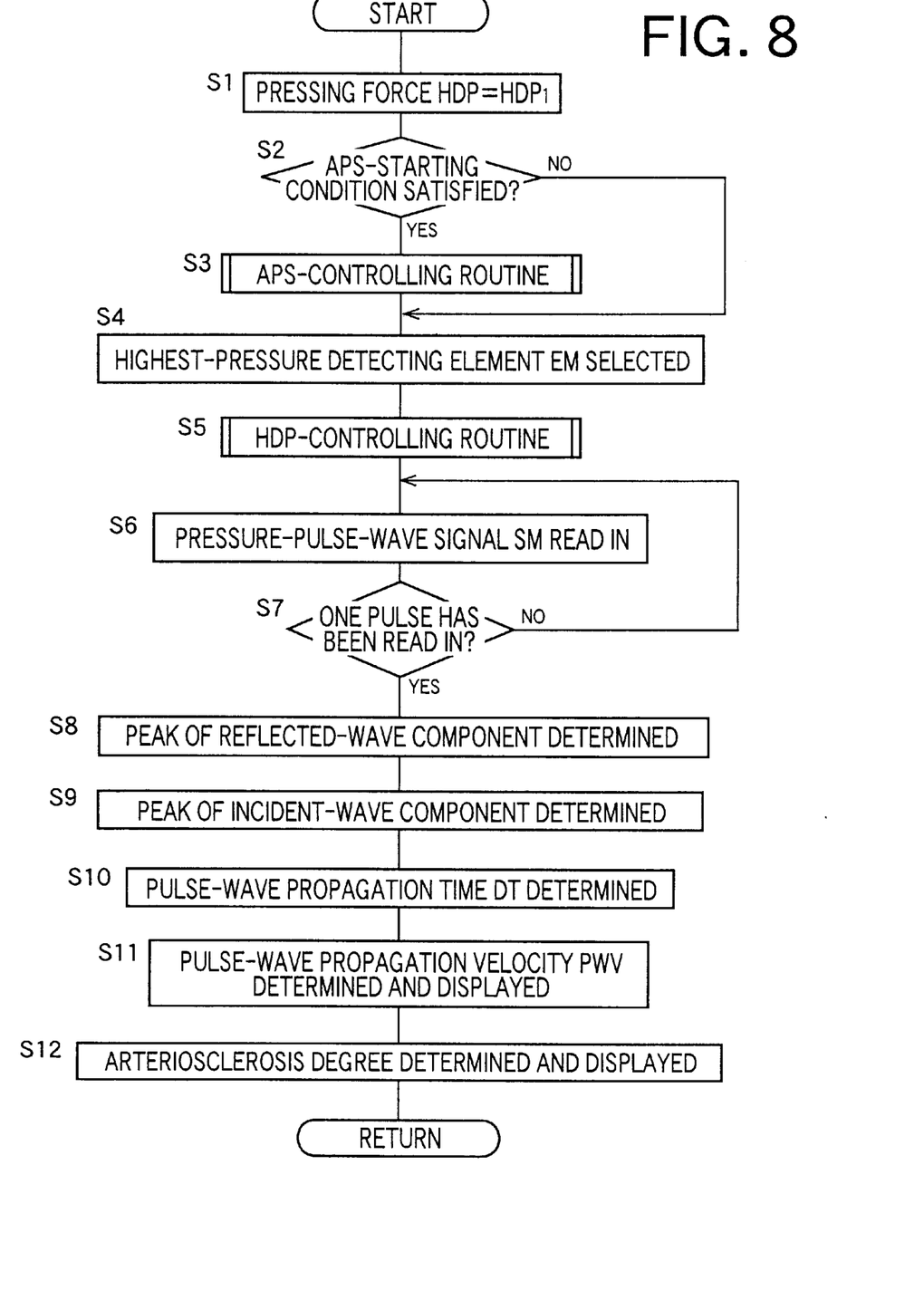
FIG. 8 is a flow chart for explaining more concretely the control functions of the control device, shown in FIG. 6.

FIG. 8 is a flow chart representing the control functions of the control device 46 shown in FIG. 6.

In FIG. 8, the control device 46 carries out Steps S1 to S3 (hereinafter, the term "Step(s)" is omitted, if appropriate) corresponding to the optimum-pressing-position determining means 70. First, at S1, the control device operates the pressing device 38 to change the pressure in the pressure chamber 32 so that the pressing force HDP applied to the pressure-pulse-wave sensor 30 is held at the prescribed first pressing force HDP1. The first pressing force HDP1 is experimentally determined, in advance, as a pressing force HDP which assures that an S/N ratio of the carotid pulse wave wc detected by each pressure-sensing element E is high enough to allow the peak pc of the carotid pulse wave wc to be detected with considerably high accuracy.

Then, the control proceeds with S2 where the control device judges whether the prescribed pressing-position changing condition (i.e., the APS-starting condition) is satisfied, i.e., whether the highest-pressure-detecting element EM as one of the pressure-sensing elements E provided in the pressing surface 42 is located in one of the prescribed opposite end portions of the array of elements E. If a negative judgment is made at S2, the control goes to S4 and the following steps, described later.

On the other hand, if a positive judgment is made at S2, that is, if the pressing position where the pressure-pulse-wave sensor 30 is pressed against the carotid artery 22 is not appropriate, the control proceeds with S3, i.e., an APS-controlling routine. According to this APS-controlling routine, the control device determines the optimum pressing position where the highest-pressure-detecting element EM is located at substantially the middle of the array of elements E. To this end, the control device operates the pressing device 38 and the widthwise-direction moving device 40 to once move the pressure-pulse-wave sensor 30 off the body surface 26, move the pressing device 38 and the sensor 30 over a prescribed distance, and again press the sensor 30 with the prescribed pressing force HDP1. In this state, the control device again judges whether the highest-pressure-detecting element EM is located at substantially the middle of the array of elements E. S2 and S3 are repeated till a positive judgment is made at S2.

Thus, at S3, the control device positions the pressure-pulse-wave sensor 30 at the optimum pressing position. Then, the control goes to S4 where the control device selects, in this state, a new highest-pressure detecting element EM from the pressure-sensing elements E of the sensor 30. S4 is followed by S5 corresponding to the pressing-force changing means 72, where the control device carries out the HDP-controlling routine in which the pressing force HDP applied by the pressing device 38 to the sensor 30 is continuously increased from the first pressing force HDP1. During this increasing of the pressing force HDP, the control device determines an optimum pressing force HDPO based on a judgment about whether a pulse pressure PP of each of successive heartbeat-synchronous pulses of the carotid pulse wave wc detected by the highest-pressure detecting element EM selected at S4 is not smaller than the prescribed lower-limit pulse pressure $PP_L$. Then, the control device maintains the pressing force HDP applied to the pressure-pulse-wave sensor 30, at the thus determined optimum pressing force HDPO.

Then, the control goes to S6 where the control device reads in the pressure-pulse-wave signal SM supplied from the highest-pressure detecting element EM of the pressure-pulse-wave sensor 30 and, then at S7, the control device judges whether the control device has read in one heartbeat-synchronous pulse of the pressure-pulse-wave signal SM, e.g., by judging whether the control device has read in a rising point of a heartbeat-synchronous pulse of the carotid pulse wave that follows a rising point of its preceding heartbeat-synchronous pulse. If a negative judgment is made at S7, S6 and the following steps are repeated to continue reading in the pressure-pulse-wave signal SM.

Meanwhile, if a positive judgment is made at S7, the control goes to S8 corresponding to the reflected-wave-peak detecting means 76, where the control device determines a peak pc of the one pulse of the carotid pulse wave wc represented by the pressure-pulse-wave signal SM read in at S6, and additionally determines a time of occurrence of the peak pc as a time of occurrence of a peak pr of the reflected-wave component wr of the carotid pulse wave wc. The thus determined time of occurrence of the peak pr is stored in the RAM 52.

Then, the control goes to S9 corresponding to the incident-wave-peak determining means 74. At S9, the control device subjects, to a fourth-order differentiation treatment or analysis, a portion or length of the pressure-pulse-wave signal SM, read in at S6, that continues from a time corresponding to the rising point of the carotid pulse wave wc and to a time corresponding to the peak pc determined at S8, and thereby determines an inflection point or a maximal point occurring to the length of the signal SM. A time of occurrence of the inflection or maximal point is determined as a time of occurrence of a peak pi of the incident-wave component wi, and is stored in the RAM 52.

Subsequently, the control goes to S10 and S11 corresponding to the pulse-wave-propagation-velocity-related-information obtaining means 78. At S10, the control device determines a pulse-wave propagation time DT by subtracting the time of occurrence of the peak pi of the incident-wave wi, determined at S9, from the time of occurrence of the peak pr of the reflected-wave wr, determined at S8. Subsequently, at S11, the control device determines, according to the above-indicated Expression (1), a pulse-wave propagation velocity PWV based on the pulse-wave propagation time DT determined at S10, and operates the display device 54 to display the thus determined pulse-wave propagation velocity PWV.

Then, the control goes to S12 corresponding to the arteriosclerosis-degree determining means 80, where the control device determines a degree of arteriosclerosis of the subject, based on the pulse-wave propagation velocity PWV determined at S11, according to the relationship between pulse-wave propagation velocity PWV and degree of arteriosclerosis, shown in FIG. 7.

As is apparent from the foregoing description of the illustrated embodiment employing the flow chart of FIG. 6, the control device 46 determines, at S9 (the incident-wave-peak determining means 74) and S10 (the reflected-wave-peak determining means 76), the peak pi of the incident-wave component wi, and the peak pr of the reflected-wave component wr, of the carotid pulse wave wc detected by the pressure-pulse-wave sensor 30. In addition, the control device determines, at S10 and S11 (the pulse-wave-propagation-velocity-related-information obtaining means 78), the pulse-wave-propagation time DT by determining the time difference between the peak pi of the incident-wave component wi and the peak pr of the reflected-wave component wr, and determines the pulse-wave-propagation velocity PWV by substituting the thus determined pulse-wave-propagation time DT for the variable DT of Expression 1. Thus, the present apparatus 10 can measure the pulse-wave-propagation velocity PWV by using the single, pressure-pulse-wave detecting probe 12.

In addition, in the illustrated embodiment employing the flow chart of FIG. 6, the control device 46 determines, at S12 (the arteriosclerosis-degree determining means 80), the degree of arteriosclerosis of the subject, based on the pulse-wave propagation velocity PWV determined at S11 (the pulse-wave-propagation-velocity-related-information obtaining means 78), according to the relationship between degree of arteriosclerosis and pulse-wave propagation velocity PW, shown in FIG. 7, and operates the display device 54 to display the thus determined arteriosclerosis degree. Thus, the present apparatus 10 can directly evaluate a hardness of the arteries of the subject as the arteriosclerosis degree determined at S11.

While the present invention has been described in its preferred embodiment by reference to the drawings, it is to be understood that the invention may otherwise be embodied.

For example, in the illustrated pulse-wave-propagation-velocity-related-information obtaining apparatus 10, the pressure-pulse-wave detecting probe 12 is worn on the neck 14 of the living subject to detect the carotid pulse wave wc, and the pulse-wave propagation velocity PWV is determined based on the detected carotid pulse wave wc. However, a pulse-wave propagation velocity PWV may be determined based on a different pulse wave than the carotid pulse wave wc; such as a brachial pulse wave detected from an upper arm of a living subject, a radial pulse wave detected from a wrist of a subject, or a femoral pulse wave detected from a femur of a subject.

The present invention may be embodied with other changes without departing from the spirit of the invention.

What is claimed is:

1. An apparatus for obtaining information related to a velocity at which a pulse wave propagates in a living subject, the apparatus comprising:

a pulse-wave sensor which is adapted to be worn on a body portion of the subject and detects the pulse wave from the body portion;

an incident-wave-peak determining means for determining a peak of an incident-wave component which is contained in the pulse wave detected by the pulse-wave sensor;

a reflected-wave-peak determining means for determining a peak of a reflected-wave component which is contained in the pulse wave detected by the pulse-wave sensor;

an information obtaining means for obtaining the information based on a time difference between the peak of the incident-wave component determined by the incident-wave-peak determining means and the peak of the reflected-wave component determined by the reflected-wave-peak determining means; and an arteriosclerosis-degree determining means for determining a degree of arteriosclerosis of the subject, based on the information obtained by the information obtaining means, according to a prescribed relationship between information related to velocity of propagation of pulse wave and degree of arteriosclerosis.

2. An apparatus according to claim 1, wherein the reflected-wave-peak determining means comprises:

means for differentiating the pulse wave detected by the pulse-wave sensor; and means for determining, as the peak of the reflected-wave component, a maximal point of the pulse wave.

3. An apparatus according to claim 1, further comprising a display device which displays the information obtained by the information obtaining means.

4. An apparatus according to claim 1, further comprising a display device which displays the degree of arteriosclerosis determined by the arteriosclerosis-degree determining means.

5. An apparatus according to claim 1, wherein the pulse-wave sensor comprises a pressure-pulse-wave sensor which is adapted to be pressed against an artery of the subject and detects, as the pulse wave, a pressure pulse wave produced from the artery.

6. An apparatus according to claim 5, wherein the pressure-pulse-wave sensor detects the pressure pulse wave produced from the artery selected from the group consisting of a carotid artery, a brachial artery, a radial artery, and a femoral artery.

7. An apparatus according to claim 5, wherein the pressure-pulse-wave sensor comprises a plurality of pressure-sensing elements each of which can detect the pressure pulse wave produced from the artery, and a pressing surface in which the pressure-sensing elements are arranged in at least one array such that in a state in which the pressure-pulse-wave sensor is worn on the body portion and the press surface is pressed against a surface of the body portion, the array of the pressure-sensing elements crosses over the artery and at least one of the pressure-sensing elements is positioned right above the artery.

8. An apparatus according to claim 1, wherein the incident-wave-peak determining means determines the peak of the incident-wave component, by differentiating the pulse wave detected by the pulse-wave sensor.

9. An apparatus according to claim 8, wherein the incident-wave-peak determining means comprises:

means for determining a rising point and a maximal point of a heartbeat-synchronous pulse of the pulse wave detected by the pulse-wave sensor;

means for differentiating a portion of the pulse wave between the rising point and the maximal point; and means for determining, as the peak of the incident-wave component, an inflection point of the differentiated portion of the pulse wave.

* * * * *